United States Patent
Onkawa et al.

(10) Patent No.: US 9,694,387 B2
(45) Date of Patent: Jul. 4, 2017

(54) GAS SENSOR ELEMENT, GAS SENSOR, AND METHOD OF MANUFACTURING GAS SENSOR ELEMENT

(71) Applicant: NGK SPARK PLUG CO., LTD., Nagoya-shi, Aichi (JP)

(72) Inventors: Masaki Onkawa, Konan (JP); Shun Sakuma, Inuyama (JP); Toru Iwano, Komaki (JP); Tatsuhiko Muraoka, Komaki (JP); Shigehiro Ohtsuka, Gifu (JP); Masaki Mizutani, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 206 days.

(21) Appl. No.: 14/525,794

(22) Filed: Oct. 28, 2014

(65) Prior Publication Data

US 2015/0114102 A1    Apr. 30, 2015

(30) Foreign Application Priority Data

Oct. 29, 2013  (JP) ................. 2013-224286

(51) Int. Cl.
*B05D 3/02* (2006.01)
*G01N 27/407* (2006.01)

(52) U.S. Cl.
CPC ....... *B05D 3/0254* (2013.01); *G01N 27/4077* (2013.01); *G01N 27/4078* (2013.01)

(58) Field of Classification Search
CPC .................. G01N 27/4077; G01N 27/4078
See application file for complete search history.

(56) References Cited

U.S. PATENT DOCUMENTS

| | | | |
|---|---|---|---|
| 2003/0159928 A1 | 8/2003 | Kojima et al. | |
| 2009/0255812 A1* | 10/2009 | Yoshida | G01N 27/4077 204/431 |
| 2010/0243445 A1* | 9/2010 | Shindo | G01N 27/4077 204/424 |
| 2011/0283775 A1* | 11/2011 | Sekiya | G01N 27/4077 73/31.05 |
| 2012/0211362 A1* | 8/2012 | Onkawa | G01N 27/4077 204/424 |

FOREIGN PATENT DOCUMENTS

JP     2003-322632 A    11/2003

* cited by examiner

*Primary Examiner* — R. A. Smith
*Assistant Examiner* — John M Royston
(74) *Attorney, Agent, or Firm* — Stites & Harbison, PLLC; Jeffrey A. Haeberlin; James R. Hayne

(57) ABSTRACT

A gas sensor element in an air/fuel ratio sensor includes an element body and a protection layer having two layers (a first layer and a second layer). The gas sensor element has at least one separation portion in the form of a space between the first layer and the second layer. The gas sensor element can temporarily accumulate, in the at least one separation portion, water which adheres to the surface of the protection layer and penetrates into the protection layer. Thus, as compared with a protection layer which is identical in thickness to the protection layer, but does not have separation portions, water adhering to the protection layer is less likely to reach the element body. Therefore, there can be restrained breakage of an end of the element body which could otherwise result from thermal shock stemming from adhesion of water.

9 Claims, 8 Drawing Sheets

GAS SENSOR ELEMENT, GAS SENSOR, AND METHOD OF MANUFACTURING GAS SENSOR ELEMENT

CROSS REFERENCE TO RELATED APPLICATIONS

The present application claims priority to Japanese Patent Application No. 2013-224286, which was filed on Oct. 29, 2013, the disclosure of which is herein incorporated by reference in its entirety.

BACKGROUND OF THE INVENTION

Field of the Invention

The present invention relates to a gas sensor element for detecting a particular gas contained in gas to be measured, a gas sensor having the gas sensor element, and a method of manufacturing the gas sensor element.

Description of Related Art

A conventionally known gas sensor having a gas sensor element for detecting a particular gas contained in gas to be measured is, for example, an oxygen sensor installed in an exhaust flow path, such as an exhaust pipe, of an internal combustion engine and utilized in controlling combustion of the internal combustion engine through detection of an oxygen concentration in exhaust gas. The oxygen sensor has, for example, a tubular metallic shell and a plate-like gas sensor element held in the metallic shell.

The gas sensor element includes a longitudinally extending plate-like element body, and a protection layer formed of a porous material and provided on the surface of the element body. The element body includes a detecting section provided in a longitudinally forward region thereof and adapted to detect a particular gas contained in gas to be measured. The protection layer is provided in a longitudinally forward end region of the element body in such a manner as to cover at least the detecting section.

The protection layer is provided for protecting the element body. Direct adhesion of condensed water may break the heated element body by thermal shock. Thus, by means of provision of the protection layer for restraining direct adhesion of condensed water or the like to the element body, breakage of the element body can be restrained. The protection layer has a certain thickness for allowing condensed water to evaporate before reaching the element body.

A known method of forming the protection layer of the gas sensor element is a dipping process in which a forward end portion of the element body is dipped in slurry prepared by mixing ceramic powder, water, and a pore-forming agent (e.g., carbon powder) (refer to Patent Document 1). The slurry applied to the element body undergoes heat treatment and becomes the protection layer.

RELATED ART DOCUMENTS

Patent Document 1 is Japanese Patent Application Laid-Open (kokai) No. 2003-322632.

BRIEF SUMMARY OF THE INVENTION

However, the above-mentioned dipping process involves the following problem: since the protection layer reduces in thickness at particular portions (particularly, in the vicinity of four vertexes of the forward end of the element body), in order to secure a sufficient thickness of the protection layer at those particular portions, dipping must be performed a plurality of times.

At this time, a plurality of times of dipping imparts an excess thickness to those portions of the protection layer which could have a sufficient thickness of the protection layer by a single time of dipping. Thus, the overall volume of the protection layer increases; accordingly, heat capacity of the protection layer increases, resulting in a wasteful increase in power consumption of a heater, along with an increase in time required for activating the sensor element.

A conceivable measure to cope with the above problem is utilization of a spraying process for spraying slurry on the surface of the element body with a spray after application of the slurry by a single time of dipping, at those particular portions which fail to have a sufficient thickness by the single time of dipping.

However, the spraying process is apt to involve waste of slurry; specifically, since slurry is sprayed in the form of mist, some slurry drops without being applied to the element body. Also, the spraying process involves the following problem: since the amount of spraying per unit time is small, and thus working time of spraying becomes long, the step of forming the protection layer becomes troublesome.

In view of the foregoing problem, an object of the present invention is to provide a gas sensor element whose protection layer is smaller in heat capacity than a conventional protection layer formed by a dipping process, and to provide a gas sensor having the gas sensor element as well as a method of manufacturing the gas sensor element.

According to one aspect of the present invention, a gas sensor element includes a rectangular-parallelepiped element body and a porous protection layer. The element body extends in a longitudinal direction and has, in its forward end region, a forward end surface and four side surfaces. The element body includes a detecting section for detecting a particular gas (i.e., a component) contained in gas (i.e., a mixture) to be measured. The porous protection layer is located (i.e., provided) on a the forward end surface and the four side surfaces of the element body in such a manner as to cover at least the detecting section.

The protection layer comprises at least two layers which differ in material or property. The two layers are a first layer formed on the element body, and a second layer formed externally of and in contact with the first layer. The gas sensor element has at least one separation portion which assumes the form of a space between the first layer and the second layer and is formed only in a forward region located forward of a place on the side surfaces of the element body where the protection layer has its largest thickness.

Furthermore, the first and second layers of the protection layer are laminated together without the separation portion intervening therebetween, on at least a portion of the forward end surface and on at least a portion of the four side surfaces in the forward region.

Since the thus-configured gas sensor element has the separation portion for separation between the first layer and the second layer in the protection layer, the gas sensor element can temporarily accumulate, in the separation portion, water which adheres to the surface of the protection layer and penetrates into the protection layer. Thus, as compared with a protection layer which is identical in thickness to the protection layer of the present invention, but does not have the separation portion, water adhering to the protection layer is less likely to reach the element body. Therefore, there can be restrained breakage of an end of the element body which could otherwise result from thermal shock stemming from adhesion of water.

That is, the protection layer of the gas sensor element can be reduced in thickness and thus in heat capacity as compared with a conventional protection layer formed by a dipping process.

Also, the separation portion is formed only in the forward region located forward of the place on the side surfaces of the element body where the protection layer has its largest thickness. By virtue of this feature, while water is temporarily accumulated in the separation portion, there can be restrained deterioration in adhesion between the protection layer (the first layer and the second layer) and the element body in a rear region located rearward of the place on the side surfaces of the element body where the protection layer has its largest thickness.

Additionally, the first layer and the second layer are laminated together without the separation portion intervening therebetween, on at least a portion of the forward end surface and on at least a portion of the four side surfaces in the forward region. Thus, although the separation portion formed in such a manner as to separate the first layer and the second layer is provided in the forward region, deterioration in adhesion between the protection layer (the first layer and the second layer) and the element body can be restrained even in the forward region.

Thus, the present invention can implement the gas sensor element having the protection layer whose heat capacity is smaller than that of a conventional protection layer formed by a dipping process.

"Property of the protection layer" appearing in the present invention is, for example, the porosity or pore size of the porous matrix of the protection layer or, in the case of a ceramic protection layer, the grain size of ceramic. The first layer and the second layer differ in at least one of these properties.

No particular limitation is imposed on the protection layer, so long as the protection layer has the first layer and the second layer in contact with each other. The protection layer may be composed of only the first layer and the second layer or may have another layer in addition to the first and second layers. Another layer is provided externally of the second layer or between the first layer and the element body.

No particular limitation is imposed on the number of the separation portions, so long as at least one separation portion is provided in the forward region. A single separation portion may be provided in the forward region, or a plurality of separation portions may be provided in the forward region.

No particular limitation is imposed on lamination of the first layer and the second layer of the protection layer on the forward end surface of the element body, so long as the first layer and the second layer are laminated together without the separation portion intervening therebetween, on at least a portion of the forward end surface. The first layer and the second layer may be laminated together without the separation portion intervening therebetween, on at least a portion of the forward end surface or on the entire forward end surface.

Furthermore, no particular limitation is imposed on lamination of the first layer and the second layer of the protection layer on the side surfaces, so long as the first layer and the second layer are laminated together without the separation portion intervening therebetween, on at least a portion of the four side surfaces in the forward region. The first layer and the second layer may be laminated together without the separation portion intervening therebetween, on a single side surface in the forward region or on each of the four side surfaces in the forward region.

In accordance with one implementation, the separation portion includes a vertex separation portion provided above (i.e. positioned over) at least one of four vertexes of a forward end of the element body in such a manner as to extend over three surfaces of the element body which define the at least one of the four vertexes.

The thus-configured gas sensor element has the vertex separation portion which is formed above at least one of four vertexes of the forward end of the element body (the thickness of the protection layer is apt to reduce at those portions of the protection layer which correspond to the four vertexes) in such a manner as to extend over three surfaces of the element body which define the one vertex and to separate the first layer and the second layer. Thus, even though the thickness of the protection layer is small in the vicinity of the vertex, there can be restrained breakage of the vertex and its vicinity of the element body which could otherwise result from thermal shock stemming from adhesion of water.

The vertex separation portion is a space for separation between the first layer and the second layer. Thus, if the range of formation of the vertex separation portion perpendicular to the thickness direction of the protection layer is excessively large, the first layer and the second layer may possibly separate from each other, since the thickness of the protection layer is relatively small. Thus, preferably, the range of formation of the vertex separation portion perpendicular to the thickness direction of the protection layer is determined so as to avoid occurrence of separation portion between the first layer and the second layer.

The "substantially rectangular-parallelepiped element body" appearing in the present invention encompasses not only a rectangular-parallelepiped element body but also an element body in the shape of a rectangular parallelepiped whose edges are chamfered. In the case of an element body having chamfered edges, "four vertexes of a forward end of the element body" indicate ridgelines defined by the chamfers and the forward end surface.

No particular limitation is imposed on provision of the separation portion, so long as the separation portion is provided above at least one of four vertexes of the forward end of the element body. The separation portion may be provided above a single vertex, or the separation portions may be provided above the four vertexes, respectively. Furthermore, the separation portions may be provided above the vertexes in one-to-one relation, or a single separation portion may be provided over a plurality of vertexes.

In accordance with another implementation, one vertex separation portion is provided above (i.e. positioned over) only one vertex.

That is, in this gas sensor element, since one vertex separation portion is provided above only one vertex, a single vertex separation portion is not formed above a plurality of vertexes. Thus, it can be avoided that a region occupied by the vertex separation portions in the protection layer becomes excessively large in relation to the forward region of the element body, whereby a sufficient contact area can be secured between the first layer and the second layer.

Thus, according to this gas sensor element, since a large contact area can be secured between the first layer and the second layer, the occurrence of separation between the first layer and the second layer can be further restrained.

In accordance with yet another implementation, the vertex separation portion is provided above (i.e. positioned over each of at least two diagonally located vertexes of the four vertexes of the forward end of the element body.

The above-mentioned gas sensor elements can employ the following configuration: the first layer and the second layer are laminated together without the separation portion intervening therebetween, on at least a portion of each of the four side surfaces of the element body in the forward region.

Through employment of the above configuration, since a region where the first layer and the second layer are in direct contact with each other without the separation portion intervening therebetween can be secured on each of the four side surfaces of the element body, adhesion between the first layer and the second layer is enhanced in the forward region, whereby separation between the element body and the protection layer (the first layer and the second layer) becomes less likely to occur.

In another implementation, a plurality (i.e., at least two) of the separation portions are provided.

Provision of a plurality of the separation portions increases a capacity for temporary accumulation of condensed water adhering to the protection layer, whereby condensed water becomes unlikely to reach the element body.

Thus, in this gas sensor element, condensed water is unlikely to reach the element body, whereby there can be restrained breakage of the element body which could otherwise result from thermal shock stemming from adhesion of water.

In yet another implementation, the element body has a heater which generates heat through application of electricity thereto, and the second layer is lower in porosity than the first layer.

In the thus-configured protection layer, since the second layer is lower in porosity than the first layer, air existing in pores of the first layer is unlikely to be released outward from the second layer. Meanwhile, air in the first layer receives heat from the heater of the element body and is thermally insulated within the protection layer. As a result, thermally insulated air can accelerate evaporation of water contained in the separation portions provided between the first layer and the second layer.

Thus, in this gas sensor element, condensed water becomes unlikely to reach the element body, whereby there can be restrained breakage of the element body which could otherwise result from thermal shock stemming from adhesion of water.

According to another aspect of the invention, a gas sensor includes the gas sensor element described above adapted to detect the particular gas contained in the gas to be measured.

The gas sensor comprises any one of the above-mentioned gas sensor elements in which there can be restrained breakage of the forward region of the element body which could otherwise result from thermal shock stemming from adhesion of water. Also, the protection layer of the gas sensor element can be smaller in thickness than a conventional protection layer formed by a dipping process and is thus smaller in heat capacity than the conventional protection layer.

Therefore, the gas sensor of the present invention can be configured to have the gas sensor element whose protection layer is smaller in heat capacity than a conventional protection layer.

Another aspect of the invention is a method of manufacturing a gas sensor element, as discussed above, which includes a substantially rectangular-parallelepiped element body extending in a longitudinal direction and having, in its forward end region, a detecting section for detecting a particular gas contained in gas to be measured, and a porous protection layer provided on a forward end surface and side surfaces of the element body in such a manner as to cover at least the detecting section.

In the gas sensor element manufactured by this manufacturing method, the protection layer comprises at least two layers which differ in material or property, and the two layers are a first layer formed on the element body, and a second layer formed externally of and in contact with the first layer.

The gas sensor element manufactured by this manufacturing method has at least one separation portion which assumes the form of a space between the first layer and the second layer and is formed only in a forward region located forward of a place on the side surfaces of the element body where the protection layer has its largest thickness. The first and second layers of the protection layer are laminated together without the separation portion intervening therebetween, on at least a portion of the forward end surface and on at least a portion of the four side surfaces in the forward region.

This method of manufacturing the gas sensor element comprises a first layer forming step, a solvent disposing step, a second layer forming step, and a heat treatment step.

In the first layer forming step, a green first layer which is to become the first layer through heat treatment is formed on the element body in such a manner as to cover at least the detecting section. In the solvent disposing step, a volatile solvent is disposed on an outer surface of the green first layer in a region where the separation portion is to be formed. In the second layer forming step, a green second layer which is to become the second layer through heat treatment is formed on the element body on which the volatile solvent remains, in such a manner as to cover at least the detecting section. In the heat treatment step, heat treatment is performed on the element body on which the green first layer and the green second layer are formed, thereby forming the first layer and the second layer. The volatile solvent is volatilized in a period from start of the solvent disposing step to end of the heat treatment step, thereby forming the separation portion.

That is, the separation portion can be formed between the first layer and the second layer in the course of a series of the following steps as a result of volatilization of the volatile solvent: the volatile solvent is disposed on the outer surface of the green first layer in a region where the separation portion is to be formed; the green second layer is formed on the element body on which the volatile solvent remains on the green first layer; and heat treatment is performed on the element body on which the green second layer is formed, thereby forming the first layer and the second layer.

According to the method of manufacturing the gas sensor element which uses the volatile solvent and comprises the first layer forming step, the solvent disposing step, the second layer forming step, and the heat treatment step, the gas sensor element having the separation portion between the first layer and the second layer can be easily manufactured.

The present invention can implement a gas sensor element whose protection layer is smaller in heat capacity than a conventional protection layer.

Also, the gas sensor of the present invention can be configured to have the gas sensor element whose protection layer is smaller in heat capacity than a conventional protection layer.

Furthermore, the method of manufacturing the gas sensor element of the present invention can manufacture the gas sensor element which has the separation portion between the first layer and the second layer and whose protection layer is smaller in heat capacity than a conventional gas sensor element.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

Embodiments of the present invention will next be described with reference to the drawings.

The following embodiments will be described while referring to a full range air/fuel ratio sensor (hereinafter, may be referred to merely as the air/fuel ratio sensor), which is a kind of oxygen sensor among gas sensors. Specifically, the following description will refer to an air/fuel ratio sensor which is attached to an exhaust pipe of an internal combustion engine and which employs a gas sensor element (detecting element) for detecting a particular gas (oxygen) contained in gas to be measured; specifically, exhaust gas, for use in air/fuel ratio feedback control in the internal combustion engine.

1. First Embodiment 1-1. Overall Configuration

Figure 1:
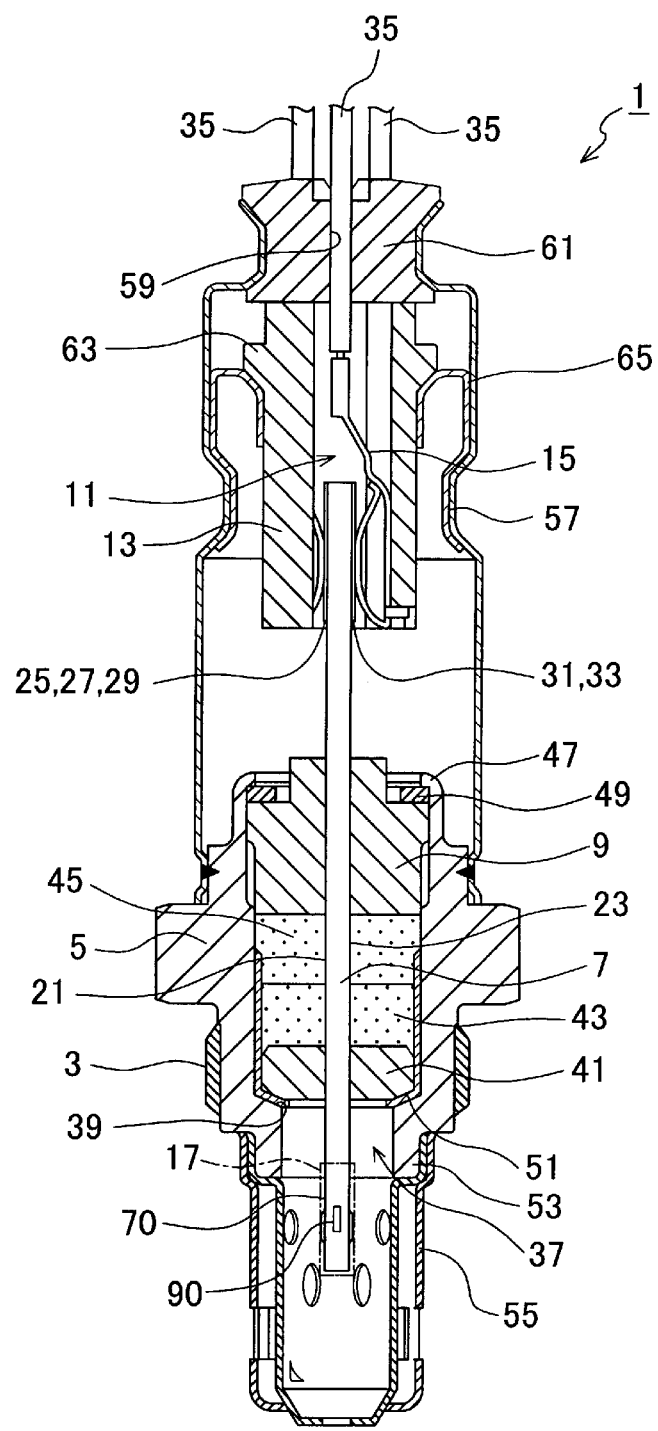
FIG. 1 is a sectional view of an air/fuel ratio sensor according to an embodiment of the present invention taken along an axial direction.

The overall configuration of an air/fuel ratio sensor which uses a gas sensor element of the present embodiment will be described with reference to FIG. 1. FIG. 1 is a sectional view showing the internal configuration of the air/fuel ratio sensor.

As shown in FIG. 1, an air/fuel ratio sensor 1 of the present embodiment includes a tubular metallic shell 5 having a threaded portion 3 formed on its outer surface and adapted to fix it to an exhaust pipe; a plate-like gas sensor element 7 extending in an axial direction (a longitudinal direction of the air/fuel ratio sensor 1, a vertical direction in FIG. 1); a tubular ceramic sleeve 9 disposed in such a manner as to radially surround the gas sensor element 7; an insulating contact member 13 (separator 13) which has an insertion hole 11 extending therethrough in the axial direction and which is disposed such that the inner wall surface of the insertion hole 11 surrounds a rear end portion of the gas sensor element 7; and five connection terminals 15 (FIG. 1 shows only two of them) disposed between the gas sensor element 7 and the separator 13.

As will be described in detail later, the gas sensor element 7 includes a rectangular-parallelepiped element body 70 extending in the longitudinal direction, and a porous protection layer 17 which covers a forward end portion of the element body 70. The element body 70 has a detecting section 90 provided in its forward end region and adapted to detect a particular gas contained in gas to be measured. Also, the gas sensor element 7 has electrode pads 25, 27, 29, 31, and 33 formed on the outer surface of its rear end portion (an upper end portion in FIG. 1, a longitudinally rear end portion); specifically, on a first main surface 21 and a second main surface 23 of the rear end portion (see FIGS. 2 and 3 for detail).

The connection terminals 15 are electrically connected to the electrode pads 25, 27, 29, 31, and 33, respectively, of the gas sensor element 7, and are also electrically connected to respective lead wires 35 extending into the sensor from outside, thereby forming electrical current paths through which electric current flows between an external device connected to the lead wires 35, and the electrode pads 25, 27, 29, 31, and 33.

The metallic shell 5 has a substantially tubular shape and is configured to have a through hole 37 extending therethrough in the axial direction and a ledge 39 protruding radially inward from the wall surface of the through hole 37. The metallic shell 5 holds the gas sensor element 7 inserted through the through hole 37 in such a manner that the detecting section 90 is disposed forward of the forward end of the through hole 37, while the electrode pads 25, 27, 29, 31, and 33 are disposed rearward of the rear end of the through hole 37.

Also, in the through hole 37 of the metallic shell 5, an annular ceramic holder 41, a talc ring 43, a talc ring 45, and the ceramic sleeve 9 are stacked rearward in this order in such a manner as to radially surround the gas sensor element 7.

A crimp packing 49 is disposed between the ceramic sleeve 9 and a rear end portion 47 of the metallic shell 5, while a metallic holder 51 for holding the talc ring 43 and the ceramic holder 41 is disposed between the ceramic holder 41 and the ledge 39 of the metallic shell 5. The rear end portion 47 of the metallic shell 5 is crimped in such a manner as to press forward the ceramic sleeve 9 through the crimp packing 49.

Furthermore, a protector 55 made of metal (e.g., stainless steel) and having a dual structure is attached to the outer circumference of a forward end portion 53 of the metallic shell 5 by, for example, welding and covers a protruding portion of the gas sensor element 7.

Meanwhile, an outer tube 57 is fixed to the outer circumference of a rear portion of the metallic shell 5. A grommet 61 having lead wire insertion holes 59 formed therein is disposed in a rear opening of the outer tube 57, and the five lead wires 35 (FIG. 1 shows three of them) are inserted through the respective lead wire insertion holes 59 and are electrically connected to the electrode pads 25, 27, 29, 31, and 33, respectively.

The separator 13 has a collar portion 63 formed along its outer circumference, and the collar portion 63 is fixed to the outer tube 57 through a holding member 65.

1-2. Configuration of Gas Sensor Element

Next, the configuration of the gas sensor element 7, which is an essential member of the present embodiment, will be described in detail with reference to FIGS. 2 to 5.

Figure 2:
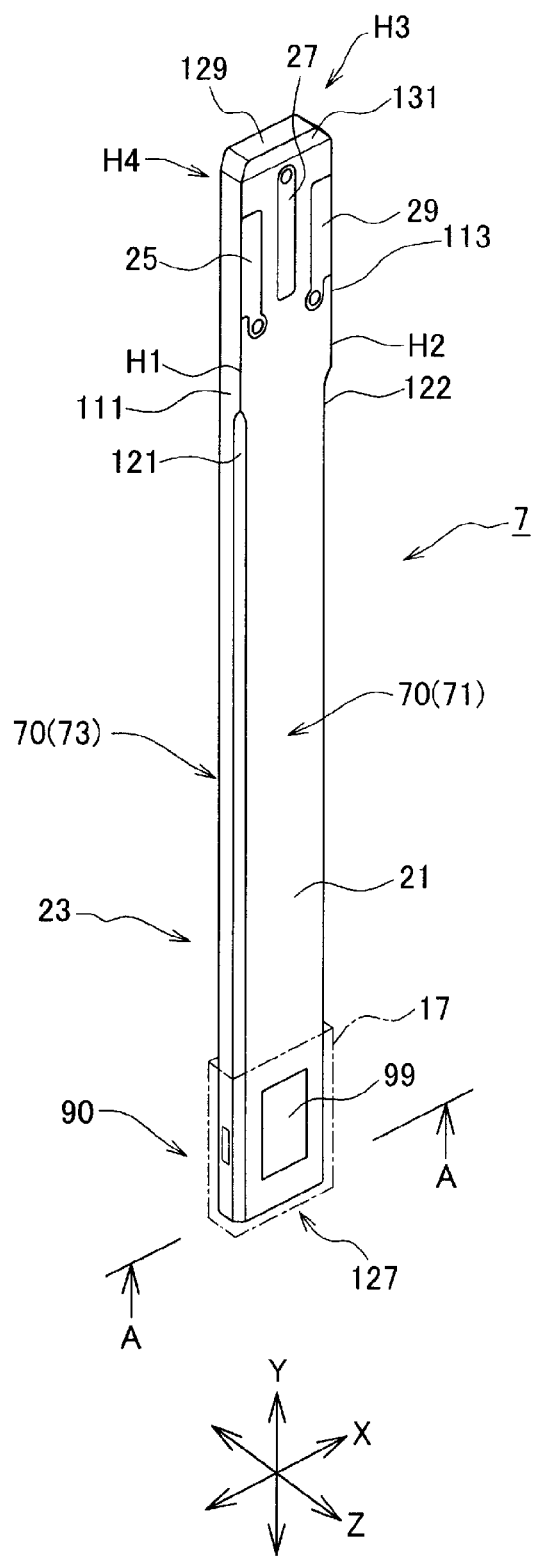
FIG. 2 is a perspective view showing a gas sensor element.

FIG. 2 is a perspective view showing the appearance of the gas sensor element 7.

As shown in FIG. 2, the gas sensor element 7 is an elongated plate member extending in the longitudinal direction (Y-axis direction). In FIG. 2, the longitudinal direction corresponds to the axial direction of the gas sensor. Also, in FIG. 2, a Z-axis direction is a thickness direction perpendicular to the longitudinal direction, and an X-axis direction is a width direction perpendicular to the longitudinal direction and to the thickness direction.

The gas sensor element 7 includes a rectangular-parallelepiped element body 70 extending in the longitudinal direction, and the porous protection layer 17 which covers a forward end portion (a lower end portion in FIG. 2) of the element body 70. The element body 70 is configured such that a plate-like element 71 extending in the longitudinal direction and a plate-like heater 73 extending in the longitudinal direction are laminated together. The element body 70 has the detecting section 90 provided in its forward end region and adapted to detect a particular gas contained in gas to be measured. The protection layer 17 is provided on a forward end surface 127 and side surfaces (the first main surface 21, the second main surface 23, a first side surface 111, and a second side surface 113) of the element body 70 in such a manner as to cover at least the detecting section 90.

Figure 3:
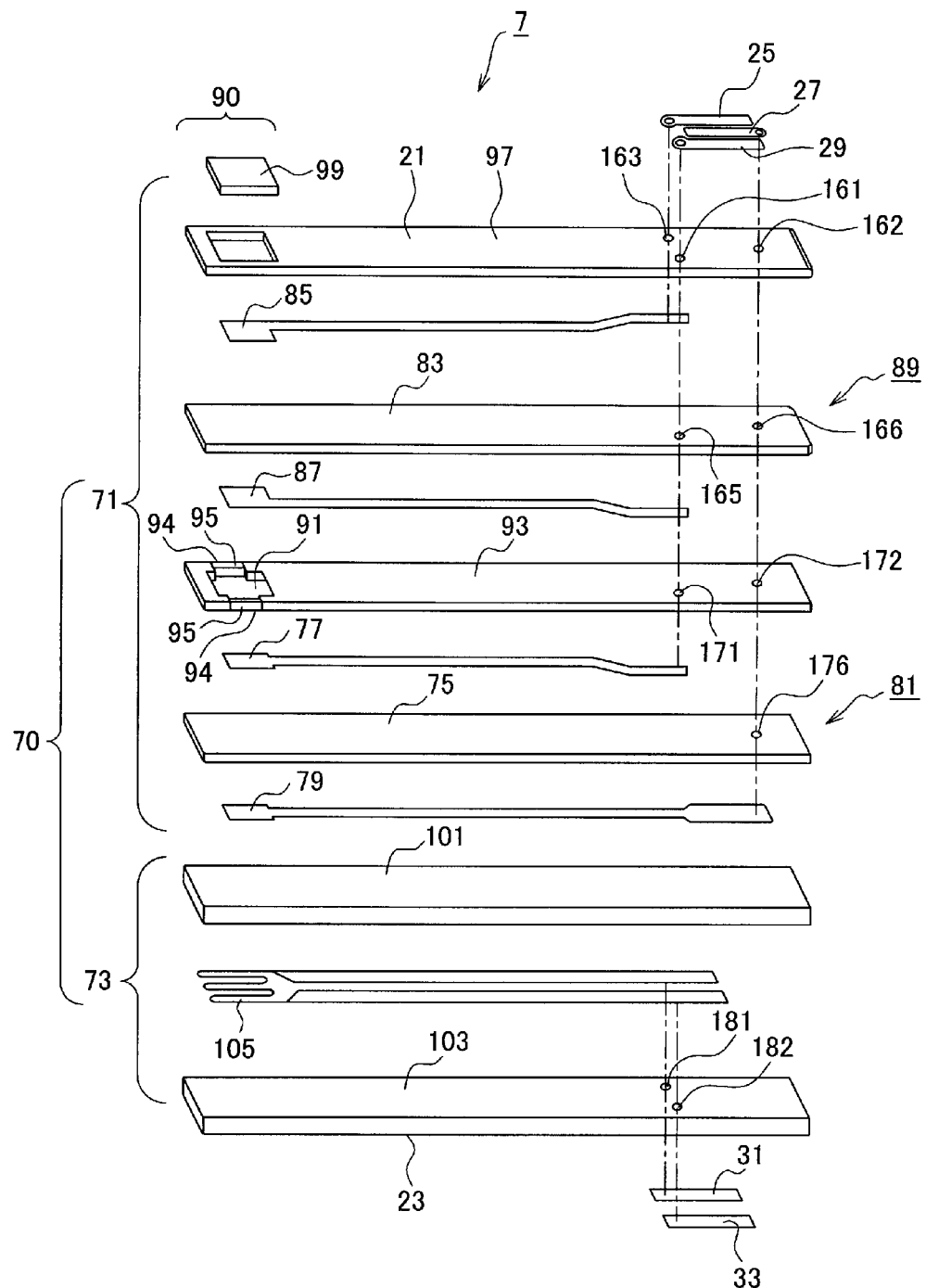
FIG. 3 is an exploded perspective view showing the gas sensor element.

FIG. 3 is an exploded perspective view showing the gas sensor element 7. FIG. 3 omits illustration of the protection layer 17 as well as a first long-side chamfer 121, a second long-side chamfer 122, a third long-side chamfer 123, and a fourth long-side chamfer 124, which will be described later.

As shown in FIG. 3 in an exploded condition, the element body 70 of the gas sensor element 7 includes the plate-like element 71 disposed on one side (upper side in FIG. 3) in a laminating direction and extending in the longitudinal direction, and the plate-like heater 73 disposed on a side (back side) opposite the element 71 and extending in the longitudinal direction.

The element 71 includes an oxygen concentration cell 81 configured such that porous electrodes 77 and 79 are formed on respective opposite sides of a solid electrolyte body 75; an oxygen pump cell 89 configured such that porous electrodes 85 and 87 are formed on respective opposite sides of a solid electrolyte body 83; and an insulating spacer 93 laminated between the two cells 81 and 89 and having a hollow gas measuring chamber 91 formed therein. The solid electrolyte bodies 75 and 83 are formed of zirconia which contains yttria as a stabilizer in solid solution, and the porous electrodes 77, 79, 85, and 87 are formed primarily of Pt.

The insulating spacer 93 in which the gas measuring chamber 91 is formed is formed primarily of alumina. The porous electrode 77 of the oxygen concentration cell 81 and the porous electrode 87 of the oxygen pump cell 89 are disposed in such a manner as to be exposed to the hollow gas measuring chamber 91.

The element 71 has two gas inlets 94 formed in respective sides thereof (sides of the insulating spacer 93). The gas inlets 94 serve as intakes of exhaust gas (gas to be measured) and communicate with the gas measuring chamber 91. Diffusion controlling portions 95 are formed in respective paths extending from the two gas inlets 94 to the gas measuring chamber 91. The diffusion controlling portions 95 are porous bodies formed of, for example, alumina and control diffusion of gas to be measured which flows into the gas measuring chamber 91. The diffusion controlling portions 95 are partially exposed from the gas inlets 94.

That is, in the gas sensor element 7, the gas inlets 94 are formed in the outermost surfaces of the element body 70 and face in two different directions, and the diffusion controlling portions 95 are exposed in the two different directions.

Furthermore, an insulating substrate 97 formed primarily of alumina is laminated on the first main surface 21 side (upper side in FIG. 3) of the element 71. The insulating substrate 97 has a ventilating portion 99 embedded therein, and the ventilating portion 99 is a porous body similar to the case of the diffusion controlling portions 95. The ventilating portion 99 allows the porous electrode 85 of the oxygen pump cell 89 to be exposed to gas to be measured.

The gas measuring chamber 91 is located in a forward end region (left end region in FIG. 3) of the element body 70. With respect to the longitudinal direction of the element 71, a region where the gas measuring chamber 91 is formed, and a region located forward of the gas measuring chamber 91 constitute the detecting section 90 for detecting oxygen.

Meanwhile, the heater 73 is formed such that a heat generating resistor pattern 105 formed primarily of Pt is sandwiched between insulating substrates 101 and 103 formed primarily of alumina.

The gas sensor element 7 has the three electrode pads 25, 27, and 29 formed on a rear end portion (right end portion in FIG. 3) of the first main surface 21, and the two electrode pads 31 and 33 formed on a rear end portion of the second main surface 23.

As shown in FIG. 3, the electrode pad 29 (right-hand electrode pad in FIG. 2) formed on the first main surface 21 is electrically connected to the porous electrode 77 of the oxygen concentration cell 81 exposed to the gas measuring chamber 91, through a through hole 161 provided in the insulating substrate 97, a through hole 165 provided in the solid electrolyte body 83, and a through hole 171 provided in the insulating spacer 93. The electrode pad 29 is also electrically connected to the porous electrode 87 of the oxygen pump cell 89 exposed to the gas measuring chamber 91, through the through hole 161 provided in the insulating substrate 97 and the through hole 165 provided in the solid electrolyte body 83. Thus, the porous electrode 77 and the porous electrode 87 are electrically connected to each other and thus have the same electrical potential.

Also, as shown in FIG. 3, another electrode pad (central electrode pad in FIG. 2) is electrically connected to the other porous electrode 79 of the oxygen concentration cell 81 through a through hole 162 provided in the insulating substrate 97, a through hole 166 provided in the solid electrolyte body 83, a through hole 172 provided in the insulating spacer 93, and a through hole 176 provided in the solid electrolyte body 75. Furthermore, as shown in FIG. 3, a further electrode pad 25 (left-hand electrode pad in FIG. 2) is electrically connected to the other porous electrode 85 of the oxygen pump cell 89 through a through hole 163 provided in the insulating substrate 97.

Also, as shown in FIG. 3, the electrode pads 31 and 33 are electrically connected to respective opposite ends of the heat generating resistor pattern 105 through through holes 181 and 182, respectively, provided in the insulating substrate 103.

Referring back to FIG. 2, since the thus-configured gas sensor element 7 is an elongated, substantially rectangular-parallelepiped plate element, it has four edges (longitudinal ridgelines) H1, H2, H3, and H4 extending its longitudinal direction (Y-axis direction in FIG. 2).

More specifically, the gas sensor element 7 has four outer walls extending its longitudinal direction; i.e., the first main surface 21 and the second main surface 23, and the first side surface 111 and the second side surface 113 in contact with the first main surface 21 and the second main surface 23.

Also, the gas sensor element 7 has the first edge H1, which is a ridgeline between the first main surface 21 and the first side surface 111; the second edge H2, which is a ridgeline between the first main surface 21 and the second side surface 113; the third edge H3, which is a ridgeline between the second main surface 23 and the second side surface 113; and the fourth edge H4, which is a ridgeline between the second main surface 23 and the first side surface 111.

Figure 4:
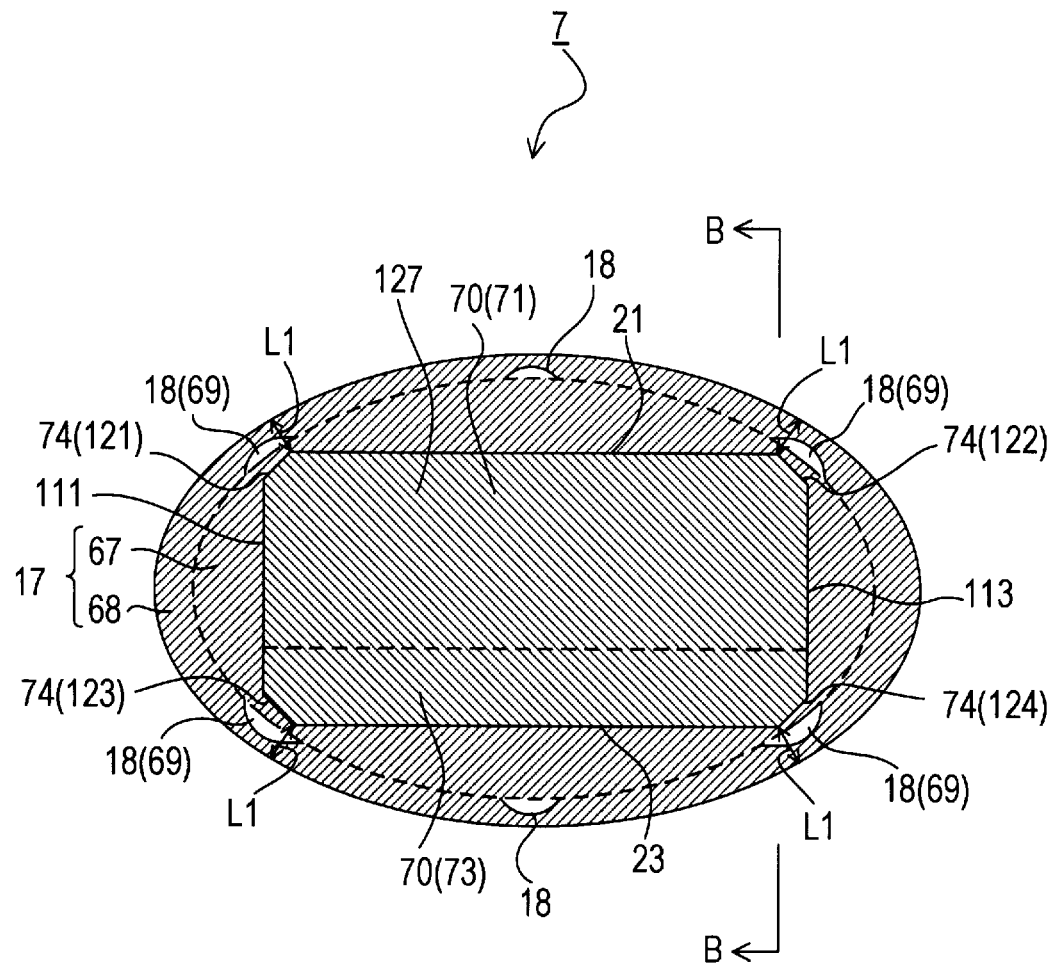
FIG. 4 is a sectional view of the gas sensor element taken along line A-A of FIG. 2.

The first edge H1, the second edge H2, the third edge H3, and the fourth edge H4 are chamfered by 0.2 mm, thereby providing a first long-edge chamfer 121, a second long-edge chamfer 122, a third long-edge chamfer 123 (see FIG. 4), and a fourth long-edge chamfer 124 (see FIG. 4). In FIG. 2, since the third long-edge chamfer 123 and the fourth long-edge chamfer 124 are invisible, their illustration with reference numerals is omitted.

The gas sensor element 7 is also chamfered at four ridgelines of its rear end surface 129 (upper end surface in FIG. 2), thereby forming rear end chamfers 131 while leaving the central rear end surface 129 (perpendicular to the longitudinal direction).

Next will be described separation portions 18 formed in the protection layer 17 of the gas sensor element 7.

Figure 5:
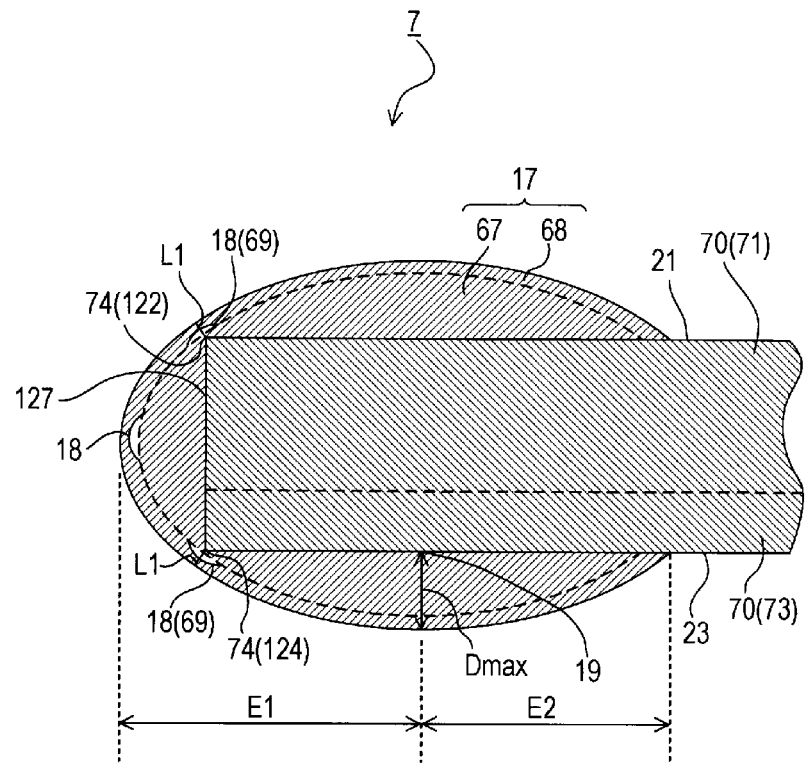
FIG. 5 is a sectional view of the gas sensor element taken along line B-B of FIG. 4.

FIG. 4 is a sectional view of the gas sensor element 7 taken along line A-A of FIG. 2. FIG. 5 is a sectional view of the gas sensor element 7 taken along line B-B of FIG. 4.

The protection layer 17 is formed of porous alumina and covers at least the detecting section 90 of the element body 70. The protection layer 17 includes a first layer 67 formed on the element body 70, and a second layer 68 formed externally of and in contact with the first layer 67.

The first layer 67 and the second layer 68 are formed of porous alumina, but differ in porosity. Specifically, the first layer 67 is higher in porosity than the second layer 68. At least one separation portion 18 is formed between the first layer 67 and the second layer 68 in the form of a space between the first layer 67 and the second layer 68. Since the separation portion 18 is a space between the first layer 67 and the second layer 68 and having a size larger than those of pores in the first layer 67 and in the second layer 68, the position of the formed separation portion 18 can be determined from a section of the protection layer 17.

The protection layer 17 has a plurality of the separation portions 18 formed therein. Furthermore, the separation portions 18 of the present embodiment include vertex separation portions 69 corresponding to four vertexes 74 of the forward end surface 127 of the element body 70. Also, the separation portions 18 of the present embodiment are formed in a region which is between the first layer 67 and the second layer 68 and which covers a central portion of the forward end surface 127 of the element body 70, as well as regions which are between the first layer 67 and the second layer 68 and which cover middle positions between the vertexes 74 of the element body 70.

Since the element body 70 of the present embodiment has the first long-edge chamfer 121, the second long-edge chamfer 122, the third long-edge chamfer 123, and the fourth long-edge chamfer 124, each of the four vertexes 74 assumes the form of a ridgeline defined by the forward end surface 127 and each of the first long-edge chamfer 121, the second long-edge chamfer 122, the third long-edge chamfer 123, and the fourth long-edge chamfer 124.

A single vertex separation portion 69 is formed in such a manner as to extend over three surfaces of the element body 70 which define the corresponding single vertex 74. For example, of the four vertex separation portions 69 shown in FIG. 4, the upper left vertex separation portion 69 is formed in such a manner as to extend over the first main surface 21, the forward end surface 127, and the first side surface 111 of the element body 70.

Also, as shown in FIG. 5, the separation portions 18 are provided on the side surfaces (the first main surface 21, the second main surface 23, the first side surface 111, and the second side surface 113) of the element body 70 only in a forward region E1 located forward of a place 19. The place 19 on the element body 70 is a place on the side surfaces (the first main surface 21, the second main surface 23, the first side surface 111, and the second side surface 113) of the element body 70 where the protection layer 17 has its largest thickness Dmax.

The gas sensor element 7 has the separation portions 18 (particularly, the vertex separation portions 69) provided above those respective vertexes 74 of the forward end surface 127 of the element body 70 at which the thickness of the protection layer 17 is apt to reduce, and extending over three surfaces of the element body 70 which define each of the vertexes 74. Thus, even though a thickness L1 of the protection layer 17 in the vicinity of the vertexes 74 is small, there can be restrained breakage of the vertexes 74 of the forward end of the element body 70 which could otherwise result from thermal shock stemming from adhesion of water.

Also, the separation portions 18 are provided only in the forward region E1 located forward of the place 19 on the four side surfaces (the first main surface 21, the second main surface 23, the first side surface 111, and the second side surface 113) of the element body 70 where the protection layer 17 has the largest thickness Dmax. This feature can restrain deterioration in adhesion between the protection layer 17 and the element body 70 in a rearward region E2 located rearward of the place 19.

Additionally, the first layer 67 and the second layer 68 of the protection layer 17 are laminated together without the separation portions 18 intervening therebetween, on at least a portion of the forward end surface 127 and on at least a portion of the four side surfaces (the first main surface 21, the second main surface 23, the first side surface 111, and the second side surface 113) in the forward region E1. Thus, even though the separation portions 18 formed to separate the first layer 67 and the second layer 68 are provided in the forward region E1, deterioration in adhesion between the protection layer 17 (the first layer 67 and the second layer 68) and the element body 70 can be restrained in the forward region E1. That is, since a sufficient contact area is secured between the element body 70 and the protection layer 17, separation of the protection layer 17 from the element body 70 becomes unlikely to arise.

1-3. Method of Manufacturing Gas Sensor

A method of manufacturing the air/fuel ratio sensor 1 of the present embodiment will be described with reference to FIGS. 6 and 7.

Figure 6:
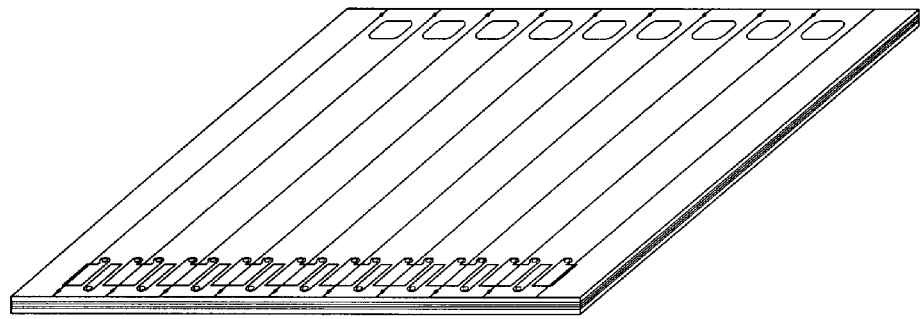
FIG. 6 is an explanatory view regarding a method of manufacturing green compacts of the gas sensor elements.

FIG. 6 is an explanatory view regarding a method of manufacturing a green compact 141 of the gas sensor elements. FIG. 7 is an explanatory view showing the gas sensor element in the middle of manufacture.

In manufacture of the gas sensor element 7, first, an uncompressed laminate is prepared by laminating together publicly known various materials used to form the gas sensor element 7; specifically, green solid electrolyte sheets used to form the solid electrolyte bodies 75 and 83 of the element 71, green insulating sheets used to form the insulating substrates 97, 101, and 103 of the heater 73 and the element 71, among others. The uncompressed laminate has green electrode pads which are to become the electrode pads 25, 27, 29, 31, and 33, among others, formed beforehand therein.

Among these materials, for example, the green solid electrolyte sheet is formed in the following manner. First, alumina powder, butyral resin, etc., are added to ceramic powder which predominantly contains zirconia. Into the resultant mixture, a mixed solvent (toluene and methyl ethyl ketone) is mixed, thereby forming slurry. The slurry is formed into a sheet by a doctor blade process, and the mixed solvent is volatilized, thereby yielding the green solid electrolyte sheet.

Also, the green insulating sheet is formed in the following manner. First, butyral resin and dibutyl phthalate are added to ceramic powder which predominantly contains alumina. Into the resultant mixture, a mixed solvent (toluene and methyl ethyl ketone) is mixed, thereby forming slurry. The slurry is formed into a sheet by the doctor blade process, and the mixed solvent is volatilized, thereby yielding the green insulating sheet.

Furthermore, green diffusion controlling portions are formed in the following manner. First, 100 mass % alumina powder and a plasticizer are wet-mixed, thereby forming slurry in which the alumina powder and the plasticizer are diffused. The plasticizer contains butyral resin and DBP. The slurry is applied to regions where the diffusion controlling portions 95 and the ventilating portion 99 are to be formed through firing, thereby forming the green diffusion controlling portions.

Then, the uncompressed laminate is compressed under a pressure of 1 MPa, thereby yielding the green compact 141 as shown in FIG. 6. A method of manufacturing the uncompressed laminate is similar to a publicly known method of manufacturing a gas sensor element; therefore, detailed description of the method is omitted.

The green compact 141 yielded through application of pressure is cut into a plurality of (e.g., ten) green laminates, each having a predetermined size substantially identical to that of the element 71 and the heater 73 of the gas sensor element 7.

Figure 7:
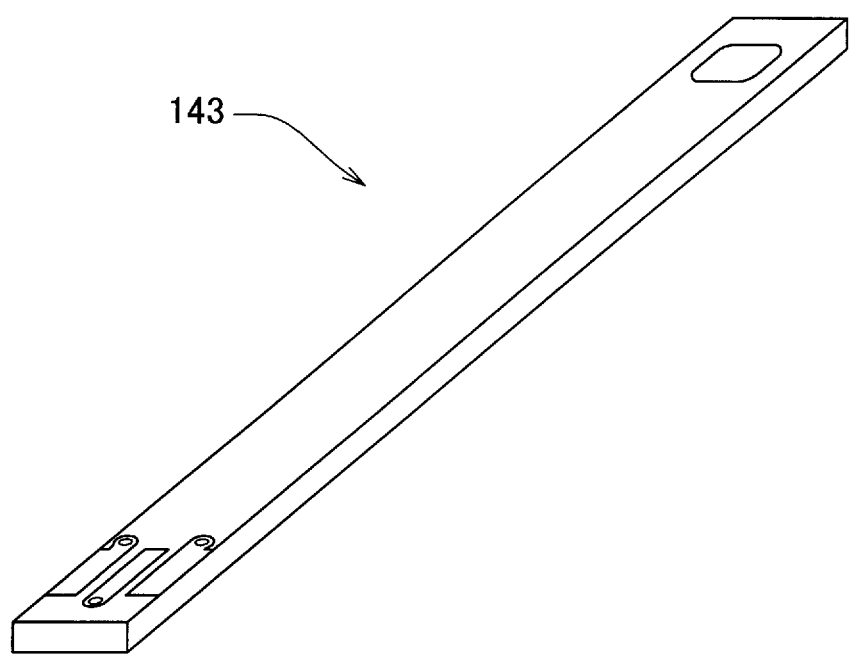
FIG. 7 is an explanatory view showing the gas sensor element in the middle of manufacture.

Subsequently, the green laminate is debindered and is, furthermore, subjected to regular firing at 1,500° C. for one hour, thereby yielding a fired laminate 143 as shown in FIG. 7.

Next, the fired laminate 143 is chamfered at its longitudinally extending four edges (the first edge H1, the second edge H2, the third edge H3, and the fourth edge H4), thereby forming the first long-edge chamfer 121, the second long-edge chamfer 122, the third long-edge chamfer 123, and the fourth long-edge chamfer 124 (see FIGS. 2 and 4). Specifically, the longitudinally extending four edges (the first edge H1, the second edge H2, the third edge H3, and the fourth edge H4) are applied to grindstone for well-known chamfering. Thus, the element body 70 is yielded.

After the element body 70 is yielded as mentioned above, a green protection layer is formed around a forward end portion of the element body 70. The green protection layer becomes the protection layer 17 having the separation portions 18 (see FIGS. 2, 4, and 5) through firing.

Figure 8:
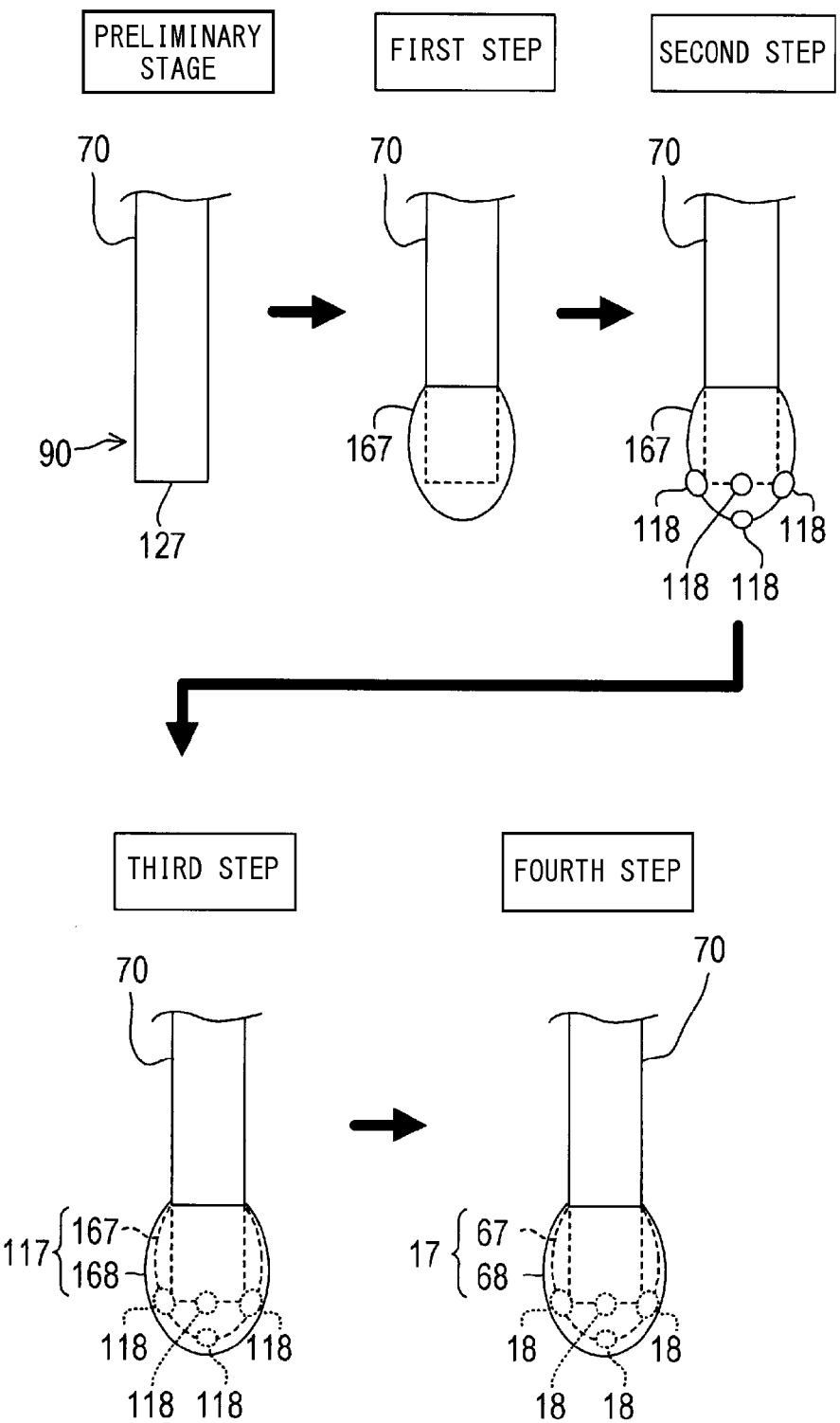
FIG. 8 is an explanatory view showing steps of forming a green protection layer.

FIG. 8 is an explanatory view showing steps of forming a green protection layer 117 on the element body 70, and yielding the protection layer 17 by performing heat treatment on the green protection layer 117.

In a stage before formation of the green protection layer 117, the element body 70 does not have a volatile solvent 118 and the green protection layer 117 thereon.

First, in the first step, a forward end portion of the element body 70 is dipped into first layer slurry in a slurry container, thereby forming a green first layer 167 on the element body 70 in such a manner as to cover at least the detecting section 90.

In the next second step, the volatile solvent 118 (e.g., ethanol, propylene glycol, or butyl carbitol) is applied to the green first layer 167 in a plurality of regions. In the present embodiment, the volatile solvent 118 is applied to the green first layer 167 at least in regions which cover the respective vertexes 74 of the forward end surface 127 of the element body 70, in a region which covers a central portion of the forward end surface 127 of the element body 70, and in regions which cover middle positions between the vertexes 74 of the element body 70.

That is, in the second step, the volatile solvent 118 is applied to regions which are to become the separation portions 18 after firing.

In the next third step, while the applied volatile solvent 118 remains, a forward end portion of the element body 70 is dipped into second layer slurry in a slurry container, thereby forming a green second layer 168 on the element body 70 in such a manner as to cover at least the detecting section 90. Subsequently, dipping is performed a predetermined number of times, thereby completing formation of the green second layer 168 having a predetermined thickness.

Thus, the green protection layer 117 having the green first layer 167 and the green second layer 168 is formed.

In the subsequent fourth step, the green protection layer 117 is subjected to heat treatment. Specifically, the element body 70 having the green protection layer 117 formed thereon is subjected to heat treatment at a temperature of 1,000° C. for three hours, thereby yielding the gas sensor element 7 on which the protection layer 17 having the separation portions 18 is formed. The green protection layer 117 (specifically, the green first layer 167 and the green second layer 168) is fired to thereby become the protection layer 17 (specifically, the first layer 67 and the second layer 68), and regions where the volatile solvent 118 is applied become the separation portions 18.

During the period from application of the volatile solvent 118 in the second step to heat treatment of the green protection layer 117 in the fourth step, the volatile solvent 118 gradually volatilizes, thereby forming the separation portions 18 in the protection layer 17 (between the first layer 67 and the second layer 68).

The thus-formed gas sensor element 7 is assembled to the metallic shell 5 in a subassembling step.

Specifically, in this subassembling step, the gas sensor element 7 manufactured by the above method is inserted into the metallic holder 51; furthermore, the gas sensor element 7 is fixed in place by the ceramic holder 41 and the talc ring 43, thereby forming a subassembly. Subsequently, while the subassembly is fixed to the metallic shell 5, and an axially rear end portion of the gas sensor element 7 is inserted through the talc ring 45 and the ceramic sleeve 9, these members are inserted into the metallic shell 5.

Then, the rear end portion 47 of the metallic shell 5 is crimped to the ceramic sleeve 9, thereby yielding a lower subassembly. The protector 55 is attached beforehand to the lower subassembly.

Meanwhile, the outer tube 57, the separator 13, the grommet 61, etc., are assembled together, thereby yielding an upper subassembly. Then, the lower subassembly and the upper subassembly are joined together, thereby yielding the air/fuel ratio sensor 1.

1-4. Comparative Test

In order to verify resistance to adhesion of water of the gas sensor element of the present invention, a water adhesion test was conducted. The test results will be described below.

In this test, a predetermined amount of water was adhered to the protection layer 17 of the gas sensor element 7 to check to see whether or not the element body 70 was broken. A sensor signal Ip output from the gas sensor element 7 was monitored. When a variation of the monitored sensor signal Ip was 1% or more in relation to the sensor signal Ip before adhesion of water, the element body 70 was considered to have broken. When a variation of the monitored sensor signal Ip was less than 1% in relation to the sensor signal Ip before adhesion of water, the element body 70 was considered to be free from breakage.

In this test, a gas sensor element having no separation portions 18 in the protection layer was prepared as a Comparative Example and was subjected to the water adhesion test. The water adhesion test was conducted on two samples (Examples 1 and 2) of the present invention which differed in the thickness of the protection layer at corners of the forward end of the gas sensor element, and on two samples (Comparative Examples 1 and 2) which differed in the thickness of the protection layer at corners of the forward end of the gas sensor element.

Water to be adhered was increased at five stages (1 μL, 2 μL, 5 μL, 7 μL, and 10 μL) in the test. When a certain sample suffered breakage of the element body at a certain amount of adhered water, the test on the sample was discontinued at that stage of the amount of water.

Table 1 shows the test results. In Table 1, "Good" appearing in the column "Result of water adhesion test" indicates that the element body is free from breakage, and "Poor" indicates that the element body was broken.

TABLE 1

| Sample | Existence of space | Result of water adhesion test | | | | | Thickness of protection layer [μm] |
| --- | --- | --- | --- | --- | --- | --- | --- |
| | | 1 μL | 2 μL | 5 μL | 7 μL | 10 μL | |
| Example 1 | Yes | Good | Good | Good | Good | Good | 352.2 |
| Example 2 | Yes | Good | Good | Good | Good | Good | 360.8 |
| Comp. Example 1 | No | Good | Poor | — | — | — | 330.4 |
| Comp. Example 2 | No | Good | Good | Poor | — | — | 351.2 |

According to the test results, Examples 1 and 2 are free from breakage of the element body 70 at all stages of the amount of adhered water (1 μL to 10 μL). Comparative Example 1 suffered breakage of the element body at an amount of adhered water of 2 μL, and Comparative Example 2 suffered breakage of the element body at an amount of adhered water of 5 μL.

Thus, as compared with a gas sensor element which does not have the separation portions 18, the gas sensor element 7 of the present invention is less likely to suffer breakage of the element body 70 which otherwise result from thermal shock stemming from adhesion of water, and therefore has excellent resistance to adhesion of water.

1-5. Effects

As described above, the gas sensor element 7 in the air/fuel ratio sensor 1 of the present embodiment includes the protection layer 17 having two layers (the first layer 67 and the second layer 68) which differ in porosity. The first layer 67 is formed on the element body 70, and the second layer 68 is formed externally of and in contact with the first layer 67.

The gas sensor element 7 has at least one separation portion 18 which assumes the form of a space between the first layer 67 and the second layer 68 and is formed only in the forward region E1 located forward of the place 19 on the side surfaces of the element body 70 where the protection layer 17 has the largest thickness Dmax.

The first layer 67 and second layer 68 of the protection layer 17 are laminated together without the separation portions 18 intervening therebetween, on at least a portion of the forward end surface 127 and on at least a portion of the four side surfaces (the first main surface 21, the second main surface 23, the first side surface 111, and the second side surface 113) in the forward region E1.

Since the thus-configured gas sensor element 7 has the separation portions 18 for separating the first layer 67 and the second layer 68 in the protection layer 17, the gas sensor element 7 can temporarily accumulate, in the separation portions 18, water which adheres to the surface of the protection layer 17 and penetrates into the protection layer 17. Thus, as compared with a protection layer which is identical in thickness to the protection layer 17, but does not have the separation portion, water adhering to the protection layer 17 is less likely to reach the element body 70. Therefore, there can be restrained breakage of the end of the element body 70 which could otherwise result from thermal shock stemming from adhesion of water.

That is, the protection layer 17 of the gas sensor element 7 can be reduced in thickness and thus in heat capacity as compared with a conventional protection layer formed by a dipping process.

Also, the separation portions 18 are formed only in the forward region E1 located forward of the place 19 on the side surfaces of the element body 70 where the protection layer 17 has the largest thickness Dmax. By virtue of this feature, while water is temporarily accumulated in the separation portions 18, there can be restrained deterioration in adhesion between the protection layer 17 (the first layer 67 and the second layer 68) and the element body 70 in the rear region E2 located rearward of the place 19 on the element body 70.

Additionally, the first layer 67 and the second layer 68 are laminated together without the separation portions 18 intervening therebetween, on at least a portion of the forward end surface 127 and on at least a portion of the four side surfaces (the first main surface 21, the second main surface 23, the first side surface 111, and the second side surface 113) in the forward region E1. Thus, although the separation portions 18 formed in such a manner as to separate the first layer 67 and the second layer 68 are provided in the forward region E1, deterioration in adhesion between the protection layer 17 (the first layer 67 and the second layer 68) and the element body 70 can be restrained even in the forward region E1.

Thus, the present embodiment can implement the gas sensor element 7 having the protection layer 17 whose heat capacity is smaller than that of a conventional protection layer formed by a dipping process.

1-6. Correspondence Between Claims and Present Embodiment

Correspondence in wording between claims and the present embodiment will be described below.

The first main surface 21, the second main surface 23, the first side surface 111, and the second side surface 113 correspond to the side surfaces of the element body. The air/fuel ratio sensor 1 corresponds to the gas sensor.

The first step corresponds to the first layer forming step; the second step corresponds to the solvent disposing step; the third step corresponds to the second layer forming step; and the fourth step corresponds to the heat treatment step.

2. Another Embodiment

While the present invention has been described with reference to the above embodiment, the present invention is not limited thereto, but may be embodied in various other forms without departing from the gist of the invention.

For example, the element body of the gas sensor element is not limited to the one in which the first edge H1, the second edge H2, the third edge H3, and the fourth edge H4 are chamfered. The element body can be configured such that none of the first edge H1, the second edge H2, the third edge H3, and the fourth edge H4 is chamfered.

Figure 9:
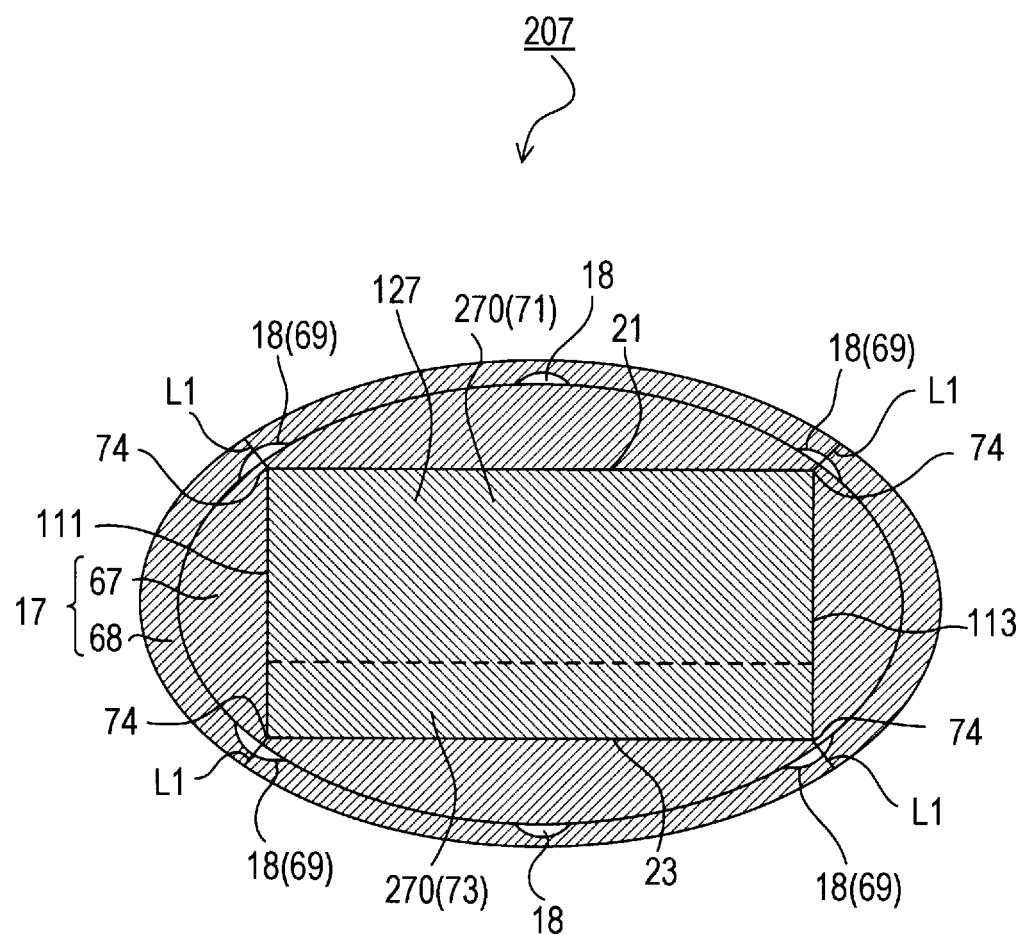
FIG. 9 is a sectional view showing a gas sensor element having an unchamfered element body.

FIG. 9 is a sectional view showing a second gas sensor element 207 having an unchamfered second element body 270, taken along the forward end surface 127 of the second element body 270. In the thus-configured second gas sensor element 207, each of the vertexes 74 assumes the form of a single point rather than a ridgeline. A plurality of the separation portions 18 are formed between the first layer 67 and the second layer 68. The separation portions 18 include the vertex separation portions 69 provided above the respective vertexes 74.

Next, in the above-mentioned gas sensor element 7, the first layer 67 and the second layer 68 differ in porosity. However, the configuration of the first layer and the second layer is not limited thereto. That is, the first layer and the second layer may differ in material or in property. The property of the protection layer is the porosity, pore size, or ceramic grain size of the porous matrix of the protection layer. The first layer and the second layer may differ in material or in at least one of the properties.

Next, each of the vertex separation portions 69 is a space between the first layer 67 and the second layer 68. Thus, if the range of formation of the vertex separation portion 69 perpendicular to the thickness direction of the protection layer 17 is excessively large, the first layer 67 and the second layer 68 may possibly separate from each other. Thus, preferably, the range of formation of the vertex separation portion 69 perpendicular to the thickness direction of the protection layer 17 is determined so as to avoid occurrence of separation between the first layer 67 and the second layer 68.

The vertex separation portion 69 is not necessarily provided above all of the four vertexes 174 of the forward end surface 127 of the element body 70 as in the case of the first embodiment. For example, the vertex separation portion 69 may be provided above three or fewer of the four vertexes 74. In certain usage of the gas sensor element, provision of a single vertex separation portion may be able to restrain thermal shock stemming from adhesion of water. In such a case, provision of a single vertex separation portion may be employed. In the case of provision of two or more vertex separation portions above the respective vertexes, the vertex separation portions may be provided at least above two diagonally located vertexes, respectively.

A single vertex separation portion is not necessarily provided above only a single vertex, but may be provided to extend between and over two vertexes.

Furthermore, the separation portion is not limited to the vertex separation portion, but may be provided in a region other than those corresponding to the four vertexes.

In the case of provision of a large number of separation portions or provision of large separation portions, preferably, a sufficient contact area is provided between the first layer and the second layer. For example, through employment of contact between the first layer and the second layer on at least half of the surface area of the forward end surface and the side surfaces, there can be implemented a gas sensor element in which separation of the second layer from the first layer is unlikely to arise.

DESCRIPTION OF REFERENCE NUMERALS

1: air/fuel ratio sensor; 7: gas sensor element; 17: protection layer; 18: separation portion; 19: place; 21: first main surface; 23: second main surface; 67: first layer; 68: second layer; 69: vertex separation portion; 70: element body; 71: element; 73: heater; 74: vertex; 90: detecting section; 117: green protection layer; 118: volatile solvent; 127: forward end surface; 167: green first layer; 168: green second layer; 207: second gas sensor element; 270: second element body; and E1: forward region.

What is claimed is:

1. A gas sensor element comprising:
   an element body having a substantially rectangular-parallelepiped shape extending along a longitudinal axis, a forward end surface through which the longitudinal axis extends, and four side surfaces adjacent to the forward end surface, and including a detecting section for detecting a particular gas; and
   a protection layer located on the forward end surface and the four side surfaces of the element body in such a manner as to cover at least the detecting section, the protection layer having a largest thickness perpendicular to the element body at a place on the four side surfaces of the element body and formed in a porous manner and at least a first layer formed directly on the element body and a second layer formed externally of and in contact with the first layer, the first layer and the second layer differing in material or property and defining at least one separation portion in the form of an open void between the first layer and the second layer and formed only in a forward region located forward of the place of the largest thickness of the protection layer;
   wherein the first layer and the second layer of the protection layer are laminated together without the separation portion intervening therebetween on at least a portion of the forward end surface and on at least a portion of the four side surfaces in the forward region.

2. The gas sensor element according to claim 1, wherein the forward end surface and the side surfaces of the element body define four vertexes, and the at least one separation portion includes a vertex separation portion positioned over at least one of the four vertexes in such a manner as to extend over the forward end surface and the four side surfaces which define the at least one of the four vertexes.

3. The gas sensor element according to claim 2, wherein the vertex separation portion positioned over only one of the four vertexes.

4. The gas sensor element according to claim 2, wherein the vertex separation portion is positioned over each of at least two diagonally located vertexes of the four vertexes.

5. The gas sensor element according to claim 1, wherein the first layer and the second layer of the protection layer are laminated together without the separation portion intervening therebetween on at least a portion of each of the four side surfaces of the element body in the forward region.

6. The gas sensor element according to claim 1, comprising at least two separation portions.

7. The gas sensor element according to claim 1, wherein the element body has a heater which generates heat through application of electricity thereto, and
the second layer is lower in porosity than the first layer.

8. A gas sensor comprising the gas sensor element of claim 1 adapted to detect the particular gas.

9. A method of manufacturing a gas sensor element which comprises an element body having a substantially rectangular-parallelepiped shape extending along a longitudinal axis, a forward end surface through which the longitudinal axis extends, and four side surfaces adjacent to the forward end surface, and including a detecting section for detecting a particular gas, and a protection layer located on the forward end surface and the four side surfaces of the element body in such a manner as to cover at least the detecting section, the protection layer having a largest thickness perpendicular to the element body at a place on the four side surfaces of the element body and formed in a porous manner and at least a first layer formed directly on the element body and a second layer formed externally of and in contact with the first layer, the first layer and the second layer differing in material or property and defining at least one separation portion in the form of an open void between the first layer and the second layer and formed only in a forward region located forward of the place of the largest thickness of the protection layer;
wherein the first layer and the second layer of the protection layer being laminated together without the separation portion intervening therebetween, on at least a portion of the forward end surface and on at least a portion of the four side surfaces in the forward region,
the method comprising:
a first layer forming step of forming, on the element body, a green first layer which is to become the first layer through heat treatment, in such a manner as to cover at least the detecting section,
a solvent disposing step of disposing a volatile solvent on an outer surface of the green first layer in a region where the separation portion is to be formed,
a second layer forming step of forming, on the element body on which the volatile solvent remains, a green second layer which is to become the second layer through heat treatment, in such a manner as to cover at least the detecting section, and
a heat treatment step of performing heat treatment on the element body on which the green first layer and the green second layer are formed, thereby forming the first layer and the second layer,
wherein the volatile solvent is volatilized in a period from start of the solvent disposing step to end of the heat treatment step, thereby forming the separation portion.

* * * * *